（12) United States Patent
Johannes et al.

(10) Patent No.: US 9,359,245 B2
(45) Date of Patent: Jun. 7, 2016

(54) VENEER CERAMIC FOR DENTAL RESTORATIONS AND METHOD FOR VENEERING DENTAL RESTORATIONS

(71) Applicant: Ivoclar Vivadent AG, Schaan (LI)

(72) Inventors: Martina Johannes, Hermsdorf (DE); Roland Ehrt, Jena (DE)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/605,327

(22) Filed: Jan. 26, 2015

(65) Prior Publication Data

US 2015/0183681 A1 Jul. 2, 2015

Related U.S. Application Data

(63) Continuation of application No. 14/054,920, filed on Oct. 16, 2013, now Pat. No. 8,987,153, which is a continuation of application No. 12/530,595, filed as application No. PCT/DE2008/000405 on Mar. 6, 2008, now Pat. No. 8,592,330.

(30) Foreign Application Priority Data

Mar. 6, 2007 (DE) .......................... 10 2007 011 337

(51) Int. Cl.
*C03C 3/068* (2006.01)
*C03C 3/112* (2006.01)
(Continued)

(52) U.S. Cl.
CPC ............... *C03C 3/112* (2013.01); *A61K 6/0005* (2013.01); *A61K 6/0094* (2013.01); *A61K 6/024* (2013.01);
(Continued)

(58) Field of Classification Search
CPC .................. C03C 10/0009; C03C 10/0027
USPC ................... 501/5, 6, 7, 65, 66, 68; 433/171, 433/191–195, 201.1, 202.1; 106/35
See application file for complete search history.

(56) References Cited

U.S. PATENT DOCUMENTS 2,684,911 A 7/1954 Stookey
3,022,180 A 2/1962 Morrissey et al.
(Continued)

FOREIGN PATENT DOCUMENTS

CA 2252660 A1 5/1999
DE 2451121 A1 5/1975
(Continued)

OTHER PUBLICATIONS

Montedo et al., Low Thermal Expansion Sintered LZSA Glass-Ceramics, American Ceramic Society Bulletin, vol. 87, No. 7, Jul. 2008, pp. 33-40.
(Continued)

*Primary Examiner* — Noah Wiese
(74) *Attorney, Agent, or Firm* — Ann M. Knab; Thad McMurray

(57) ABSTRACT

The invention is directed to starting glass compositions for veneer ceramics for dental restorations of framework ceramics comprising yttrium-stabilized zirconium dioxide. It is the object of the invention to make possible a translucent veneer ceramic which has high flexural strength as well as excellent adhesion to the framework ceramic of yttrium-stabilized zirconium dioxide. According to the invention, this object is met in a starting glass for veneer ceramics for dental restorations made of yttrium-stabilized zirconium dioxide which is produced from the following components:
a) $SiO_2$ 58.0-74.0 percent by weight
b) $Al_2O_3$ 4.0-19.0 percent by weight
c) $Li_2O$ 5.0-17.0 percent by weight
d) $Na_2O$ 4.0-12.0 percent by weight
e) $ZrO_2$ 0.5-6.0 percent by weight.

17 Claims, 3 Drawing Sheets

(51) Int. Cl.

| | |
|---|---|
| *C03C 3/085* | (2006.01) |
| *C03C 4/00* | (2006.01) |
| *C03C 10/00* | (2006.01) |
| *C04B 41/00* | (2006.01) |
| *C04B 41/50* | (2006.01) |
| *C04B 41/86* | (2006.01) |
| *A61K 6/00* | (2006.01) |
| *A61K 6/02* | (2006.01) |
| *C03C 8/14* | (2006.01) |
| *C03B 32/02* | (2006.01) |
| *C03C 3/083* | (2006.01) |
| *C03C 3/097* | (2006.01) |
| *C04B 111/00* | (2006.01) |

(52) U.S. Cl.
CPC ............... *A61K 6/025* (2013.01); *A61K 6/0215* (2013.01); *A61K 6/0255* (2013.01); *C03B 32/02* (2013.01); *C03C 3/083* (2013.01); *C03C 3/085* (2013.01); *C03C 3/097* (2013.01); *C03C 4/0021* (2013.01); *C03C 8/14* (2013.01); *C03C 10/0027* (2013.01); *C04B 41/009* (2013.01); *C04B 41/5023* (2013.01); *C04B 41/86* (2013.01); *C04B 2111/00836* (2013.01)

(56) References Cited

U.S. PATENT DOCUMENTS

| | | |
|---|---|---|
| 3,252,778 A | 5/1966 | Goodmann et al. |
| 3,287,201 A | 11/1966 | Chisholm et al. |
| 3,006,775 A | 10/1969 | Chen |
| 3,679,464 A | 7/1972 | Eppler |
| 3,804,608 A | 4/1974 | Gaskell et al. |
| 3,816,704 A | 6/1974 | Borom et al. |
| 3,977,857 A | 8/1976 | Mattox |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,755,488 A | 7/1988 | Nagashima |
| 4,798,536 A | 1/1989 | Katz |
| 5,176,961 A | 1/1993 | Crooker et al. |
| 5,217,375 A | 6/1993 | Oden et al. |
| 5,219,799 A | 6/1993 | Beall et al. |
| 5,507,981 A | 4/1996 | Petticrew |
| 5,618,763 A | 4/1997 | Frank et al. |
| 5,641,347 A | 6/1997 | Grabowski et al. |
| 5,698,482 A | 12/1997 | Frank |
| 5,872,069 A | 2/1999 | Abe |
| 5,874,376 A | 2/1999 | Taguchi et al. |
| 5,968,856 A | 10/1999 | Schweiger et al. |
| 6,022,819 A | 2/2000 | Panzera et al. |
| 6,048,589 A | 4/2000 | Suzuki |
| 6,106,747 A | 8/2000 | Wohlwend |
| 6,119,483 A | 9/2000 | Takahashi et al. |
| 6,174,827 B1 | 1/2001 | Goto |
| 6,270,876 B1 | 8/2001 | Abe et al. |
| 6,280,863 B1* | 8/2001 | Frank ............... C03C 4/0021 106/35 |
| 6,376,397 B1 | 4/2002 | Petticrew |
| 6,420,288 B2 | 7/2002 | Schweiger et al. |
| 6,514,893 B1 | 2/2003 | Schweiger et al. |
| 6,517,623 B1* | 2/2003 | Brodkin ............... C03B 19/06 106/35 |
| 6,593,257 B1 | 7/2003 | Nagata |
| 6,802,894 B2* | 10/2004 | Brodkin ............... C03B 19/06 106/35 |
| 7,162,321 B2 | 1/2007 | Luthardt et al. |
| 7,166,548 B2 | 1/2007 | Apel et al. |
| 7,316,740 B2 | 1/2008 | Schweiger et al. |
| 7,452,836 B2 | 11/2008 | Apel et al. |
| 7,867,930 B2 | 1/2011 | Apel et al. |
| 7,867,933 B2 | 1/2011 | Apel et al. |
| 7,993,137 B2 | 8/2011 | Apel et al. |
| 2002/0009600 A1 | 1/2002 | Peng |
| 2002/0022563 A1 | 2/2002 | Schweiger et al. |
| 2005/0079391 A1* | 4/2005 | Ikenishi ............... C03C 3/083 428/846.9 |
| 2009/0023574 A1 | 1/2009 | Höland et al. |
| 2009/0038344 A1 | 2/2009 | Apel et al. |
| 2009/0038508 A1 | 2/2009 | Apel et al. |
| 2009/0256274 A1 | 10/2009 | Castillo |
| 2011/0030423 A1 | 2/2011 | Johannes et al. |
| 2012/0094822 A1 | 4/2012 | Castillo |
| 2012/0148988 A1 | 6/2012 | Castillo |
| 2012/0309607 A1 | 12/2012 | Durschang et al. |

FOREIGN PATENT DOCUMENTS

| | | |
|---|---|---|
| DE | 3015529 A1 | 6/1980 |
| DE | 19647739 A1 | 3/1998 |
| EP | 0231773 A1 | 8/1987 |
| EP | 774933 B1 | 6/2000 |
| EP | 1422210 A1 | 5/2004 |
| EP | 1505041 A1 | 9/2005 |
| GB | 2284655 A | 6/1995 |
| JP | 11074418 A | 3/1999 |
| JP | 2001035417 A | 2/2001 |
| JP | 2005062832 A | 3/2005 |
| WO | 0247616 A2 | 6/2002 |
| WO | 03035014 A1 | 1/2003 |

OTHER PUBLICATIONS

Stookey, S.D., "Chemical Machining of Photosensitive Glass," Ind. Eng. Chem. 45:115-118 (1993).

Von Clausburch et al., "The effect of P2O5 on the Crystallization and Microstructure of Glass-Ceramics in the SiO2—Li2O—K2O—ZnO—P2O5 System," J. of Non-Crystalline Solids 263&264, pp. 388-394 (2000).

Giassi et al., "Injection Moulding of LiO2—ZrO2—SiO2—Al2O3 (LZSA) Glass Ceramics," Glass Technol., 46(3), 277-280. (2005).

Borom, et al., "Strength and Microstructure in Lithium Disilicate Glass Ceramics," J. Am Ceram Soc 58 (9-10): 285-391 (1975).

Oliveira et al., "Sintering and Crystallization of a Glass Powder in the Li2O—ZrO2—SiO2 System," J. Am. Ceramic Soc. 81(3): 777-780 (1998).

Von Clausburch et al., "Effect of ZnO on the Crystallization, Microstructure, and Properties of Glass-Ceramics in the SiO2—Li2O—K2O—P2O5 System," Glastech. Ber. Glass Sci. Technol. 74(8): 223-229 (2001).

Sundh et al., "Fracture resistance of yttrium oxide partially-stabilized zirconia all-ceramic bridges after veneering and mechanical fatigue testing," Dental Materials 2005, vol. 21, pp. 476-482.

\* cited by examiner

VENEER CERAMIC FOR DENTAL RESTORATIONS AND METHOD FOR VENEERING DENTAL RESTORATIONS

This present application is a continuation application of U.S. application Ser. No. 14/054,920, filed Oct. 16, 2013, which is a continuation application of U.S. application Ser. No. 12/530,595, filed Oct. 20, 2010, now U.S. Pat. No. 8,592, 330, which is the U.S. National Stage filing under 35 U.S.C. §371 of International Application No. PCT/DE2008/000405 filed Mar. 6, 2008 and published on Sep. 12, 2008 as Publication No. WO 2008/106958 A2, which claims priority to DE Application No. 102007011337.6, filed Mar. 6, 2007, all of which are hereby incorporated by reference.

BACKGROUND OF THE INVENTION

1. Field of the Invention

The invention is directed to veneer ceramics for dental restorations in which the framework ceramic is made of yttrium-stabilized zirconium dioxide.

2. Description of the Related Art

Yttrium-stabilized zirconium dioxide is a high-performance material of extremely high strength that is used to an increasing extent in restorative dentistry for framework ceramics for crowns, inlays, and bridges. The application of veneer ceramics is required for fine adjustment to the diversity of natural teeth. Up to the present, veneer ceramics have presented a weak point in the ability of the restored teeth to withstand stress.

Veneer ceramics should permit excellent shaping, be conformable to the adjacent teeth with respect to coloring, be highly resistant to chemicals, have a high flexural strength even after a directed heat treatment, and be characterized by outstanding adhesion to the framework ceramic.

Powders or pastes are generally used as starting materials for producing the veneer ceramics. The properties of the veneer ceramic are determined by the chemical and crystallographic features as well as by the grain size of the starting materials.

According to U.S. Pat. No. 4,798,536 A, leucite-containing dental porcelains are produced by means of the fused glass. The leucite content is in the range of 35 to 60 percent by weight. The high coefficient of expansion of the leucite-containing dental porcelain of 13 to $15 \times 10^{-6}$/K is used for veneering metal crowns. The flexural strength of the veneer ceramic with leucite crystals is 80 MPa.

The use of lithium disilicate is proposed for a restorative tooth prosthesis in U.S. Pat. No. 4,189,325 A. This reference concentrates on the material system of $Li_2O$—CaO—$Al_2O_3$—$SiO_2$. The nucleating agents $Nb_2O_5$ and Pt are added to promote crystallization.

U.S. Pat. No. 4,515,634 A suggests the addition of the nucleating agent $P_2O_5$ to the basic system of $Li_2O$—CaO—$Al_2O_3$—$SiO_2$ in order to improve nucleation and crystallization.

Laid Open Application DE 197 50 794 A1 describes the use of lithium disilicate glass ceramics use in the hot pressing method. However, it has been shown that application of this method results in insufficient edge strength of the restored tooth and increased tool wear during finishing.

DE 103 36 913 A1 suggests a two-stage fabrication of the tooth to be restored. In the first step, lithium metasilicate is crystallized and is mechanically worked to form dental products. The lithium metasilicate is converted to the stronger lithium disilicate by a second heat treatment. Accordingly, the restored tooth is made entirely of glass ceramic with lithium disilicate crystals.

German Patent DE 196 47 739 C2 describes a sinterable lithium disilicate glass ceramic and glass. The starting material is sintered to form blanks. These blanks are pressed at 700° C. to 1200° C. to form dental products. The described lithium disilicate glass ceramic shows only a slight reaction to the adjacent casting investment during plastic deformation.

EP 1 235 532 A1 describes a method for producing a high-strength ceramic dental prosthesis based on yttrium-stabilized zirconium dioxide. The framework ceramics produced by this method have 4-point flexural strengths greater than 1200 MPa.

SUMMARY OF THE INVENTION

It is the object of the invention to make possible a translucent veneer ceramic which has high flexural strength as well as excellent adhesion to the framework ceramic of yttrium-stabilized zirconium dioxide.

DESCRIPTION OF THE DRAWINGS

The invention will be described more fully in the following with reference to embodiment examples. The drawings show.

DETAILED DESCRIPTION

Figure 1:
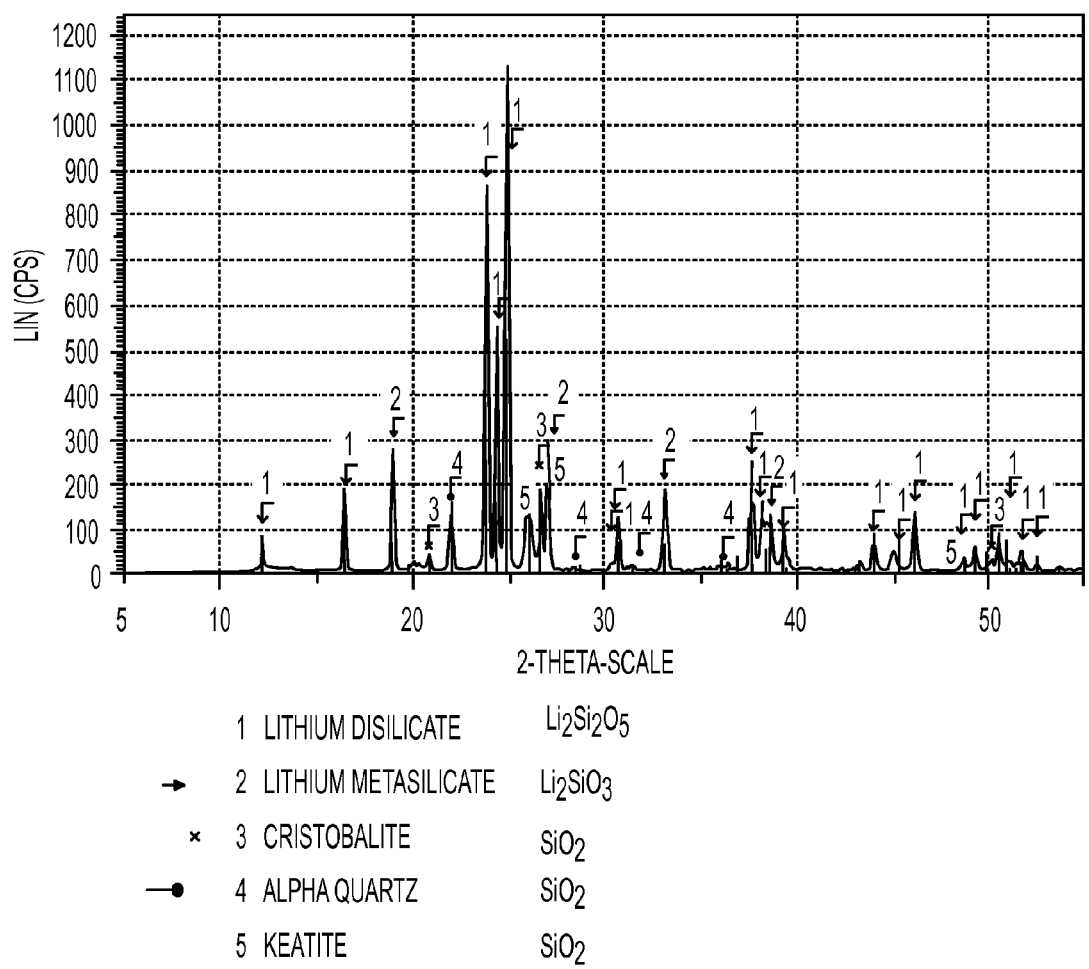
FIG. 1 an x-ray diffractogram (XRD) after the solid state reaction of lithium oxide and silicon dioxide (4 hours at 940° C.)

According to the invention, the objects are met in a veneer ceramic for dental restorations made of yttrium-stabilized zirconium dioxide which is produced by the following components:

a) $SiO_2$ 58.0-74.0 percent by weight
b) $Al_2O_3$ 4.0-19.0 percent by weight
c) $Li_2O$ 5.0-17.0 percent by weight
d) $Na_2O$ 4.0-12.0 percent by weight
e) $ZrO_2$ 0.5-6.0 percent by weight It can be advantageous when another nucleating agent, e.g., $TiO_2$, is added within limits of 0.2 to 8.0 percent by weight in addition to the nucleating agent $ZrO_2$.

The veneer ceramic is applied as powdered starting glass with crystalline additions or without separate crystalline additions and is sintered onto dental products of yttrium-stabilized zirconium dioxide by means of a defined temperature program in the range of 800° C. to 940° C. and crystallized in a controlled manner.

Surprisingly, it was shown that a very high adhesion strength to dental products of yttrium-stabilized zirconium dioxide is achieved with specific glass ceramics and a defined temperature program. The veneer ceramic is translucent and has very good resistance to chemicals. The main crystal phase of the glass ceramic comprises lithium disilicate.

Besides the powdered starting glasses of the glass ceramic, the veneer ceramic can also contain powdered crystals as starting product. By means of a defined heat treatment, the powdered veneer ceramic undergoes the processes of nucleation, sintering and fusion with the yttrium-stabilized zirconium dioxide and crystallization accompanied by the formation of microcrystals.

Also, powdered lithium disilicate is preferably added to the starting glasses. The lithium disilicate can be produced by a solid state reaction.

The addition of $TiO_2$ promotes the process of nucleation and crystallization of lithium disilicate. The veneer ceramic is then advantageously formed from a mixture containing the following components:

TABLE 1

| | Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| $SiO_2$ | 71.0 | 71.1 | 62.0 | 70.5 | 69.7 | 61.2 | 70.5 | 70.5 | 69.6 | 69.6 | 58.9 | 60.5 |
| $Al_2O_3$ | 9.0 | 4.9 | 17.9 | 8.9 | 4.8 | 17.7 | 4.9 | 8.9 | 8.8 | 8.8 | 17.0 | 17.5 |
| $Li_2O$ | 12.6 | 14.9 | 5.3 | 12.5 | 14.6 | 5.2 | 14.8 | 12.5 | 12.4 | 12.4 | 5.0 | 5.2 |
| $Na_2O$ | 5.4 | 3.0 | 10.9 | 5.4 | 2.9 | 10.8 | 3.0 | 5.4 | 5.3 | 5.3 | 10.4 | 10.5 |
| $TiO_2$ | | 5.0 | | | 4.9 | 1.2 | 5.0 | | | | 5.0 | 2.5 |
| $ZrO_2$ | 2.0 | 1.1 | 3.9 | 2.0 | 1.1 | 3.9 | 1.1 | 2.0 | 2.0 | 2.0 | 3.7 | 3.8 |
| $CaF_2$ | | | | 0.7 | | | 0.7 | | | | | |
| CaO | | | | | 0.6 | | | | | | | |
| $MgF_2$ | | | | | | | | 0.7 | | | | |
| $BaF_2$ | | | | | | | | | | 1.9 | | |
| BaO | | | | | | | | | 1.1 | | | |
| $P_2O_5$ | | | | | 1.4 | | | | 0.8 | | | |
| Total | 100 | 100 | 100 | 100 | 100 | 100 | 100 | 100 | 100 | 100 | 100 | 100 | a) $SiO_2$ 58.0-72.0 percent by weight
b) $Al_2O_3$ 4.0-18.0 percent by weight
c) $Li_2O$ 5.0-17.0 percent by weight
d) $Na_2O$ 4.0-11.0 percent by weight
e) $ZrO_2$ 0.5-5.5 percent by weight
f) $TiO_2$ 0.2-8.0 percent by weight Zirconium dioxide or a mixture of zirconium dioxide and titanium dioxide is used as nucleating agent for the controlled crystallization of the veneer ceramic based on lithium silicate materials. The addition of titanium dioxide promotes the conversion of lithium metasilicate to lithium disilicate.

In a preferable veneer ceramic, lithium titanium oxide silicate $Li_2TiOSiO_4$, lithium aluminum silicate (beta spodumene) and small amounts of lithium metasilicate are crystallized in addition to the lithium disilicate.

The veneer ceramic can also be formed in such a way that the crystalline portion is below 40%. In this case, the veneer ceramic is thinly applied, serves for color matching, and imparts a particular aesthetic gloss to the dental framework ceramic. The strength of the veneer ceramic can be further increased by deliberate compressive stresses.

The oxides of elements Ce, Fe, Mn, Sn, V, Cr, In, and of rare earths Pr, Nd, Sm, Eu, Tb, Dy and Er can be used as coloring or fluorescing additions.

To modify the technology, the additives $La_2O_3$, $B_2O_3$, $P_2O_5$, CaO, MgO, ZnO and fluoride can be added independently from one another in concentrations of up to 4.0 percent by weight at most.

To produce the veneer ceramic, nucleation is carried out in the temperature range of 500° C. to 680° C., and the melting and crystallization is carried out in the temperature range of 800° C. to 940° C. The nucleation and crystallization processes can be interrupted in that the veneer ceramic is cooled to room temperature between nucleation and crystallization, stored, and then heated to the crystallization temperature.

The adhesion strength between the yttrium-stabilized zirconium dioxide and the veneer ceramic is determined by flexural testing. For this purpose, the powdered veneer ceramic is applied to the end face of two round rods of zirconium dioxide and subjected to the defined heat treatment. The adhesion strength is determined by the three point flexural test.

Veneer ceramics with an adherence to zirconium dioxide of at least 150 MPa are preferred.

Twelve compositions are shown in Table 1 as embodiment examples of the veneer ceramics according to the invention.

Figure 2:
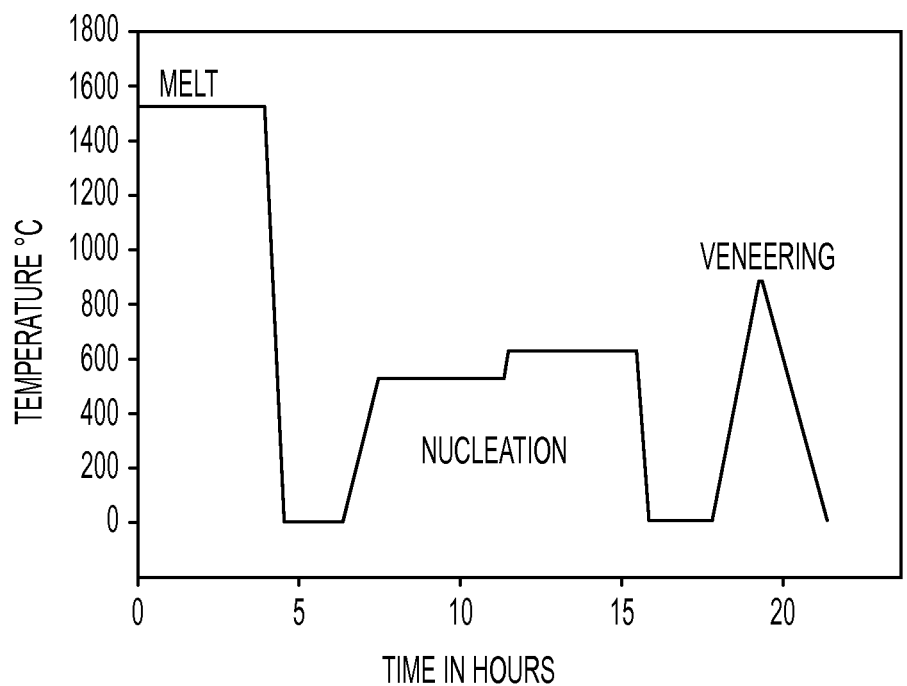
FIG. 2 a typical temperature curve for the production of the veneer ceramic.

The starting glasses were fused in platinum or platinum-rhodium crucibles at a temperature of 1530° C. and cast in water to produce a frit (FIG. 2).

To promote the controlled crystallization, the fritted starting glasses are tempered for approximately 4 hours at 580° C.±100° C. and powdered after cooling. The grain size used ranges from 0.6 μm to 20 μm.

Powdered lithium disilicate can be added to the starting glasses. The lithium disilicate is produced by a solid state reaction.

FIG. 1 shows the x-ray diffractogram (XRD) of the lithium disilicate produced by the solid state reaction.

The moistened starting materials are applied to the dental framework ceramic of yttrium-stabilized zirconium dioxide as veneer ceramic, melted at 890° C.±50° C. and crystallized in a controlled manner.

FIG. 2 shows the typical temperature curve during the production process for the veneer ceramic.

All twelve examples of the veneer ceramics listed in Table 1 are translucent.

The optical effect and the mechanical resistance of the veneer ceramics are influenced by the structure of the veneer ceramic as well as by the interaction of the veneer ceramic and framework ceramic.

The coefficient of expansion (a) of the veneer ceramic and of the framework ceramic of yttrium-stabilized zirconium dioxide (TZ3Y) must be adapted to one another.

Based on the examples in Table 1, the coefficients of expansion (a) of the veneer ceramics are shown and compared with yttrium-stabilized zirconium dioxide in Table 2.

TABLE 2

| | Examples | | | | | |
|---|---|---|---|---|---|---|
| | 1 | 2 | 3 | 6 | 11 | $ZrO_2$ |
| $\alpha_{50\text{-}300°\ C.} \times 10^{-6}/K$ | 8.9 | 8.7 | 8.9 | 8.9 | 8.7 | 9.6 |
| $\alpha_{50\text{-}500°\ C.} \times 10^{-6}/K$ | 9.8 | 9.8 | 9.8 | 9.6 | 9.3 | 9.8 |

The adhesion strength between the framework ceramic of yttrium-stabilized zirconium dioxide and the veneer ceramic was determined by the three point flexural test. For this purpose, the powder of the veneer ceramic was applied between two cylindrical samples of zirconium dioxide and subjected to a heat treatment corresponding to FIG. 2.

Table 3 shows the adhesion strength for selected samples, where α=adhesion strength in MPa based on the three point flexural test and m=Weibull parameter.

TABLE 3

| Examples | 1 | 2 | 3 | 12 |
|---|---|---|---|---|
| α MPa | 162.1 | 183.1 | 173.4 | 172.4 |
| m | 7.6 | 13.2 | 3.5 | 4.4 |

Depending on the composition and heat treatment, the course of nucleation and crystallization may differ in the veneer ceramics with high adhesion strength according to the invention.

Referring to Table 1 and a temperature of 890° C.±50° C., the examples of veneer ceramics 1, 4, 8, 9, and 10 crystallize to lithium silicate and zirconium dioxide crystal phases. The zirconium dioxide serves as a nucleating agent. The crystallization of the lithium silicate takes place in two temporal stages. First, lithium metasilicate $Li_2SiO_3$ is formed and, through the subsequent reaction with the surrounding silicate phase, lithium metasilicate is converted to lithium disilicate $Li_2Si_2O_5$.

Figure 3:
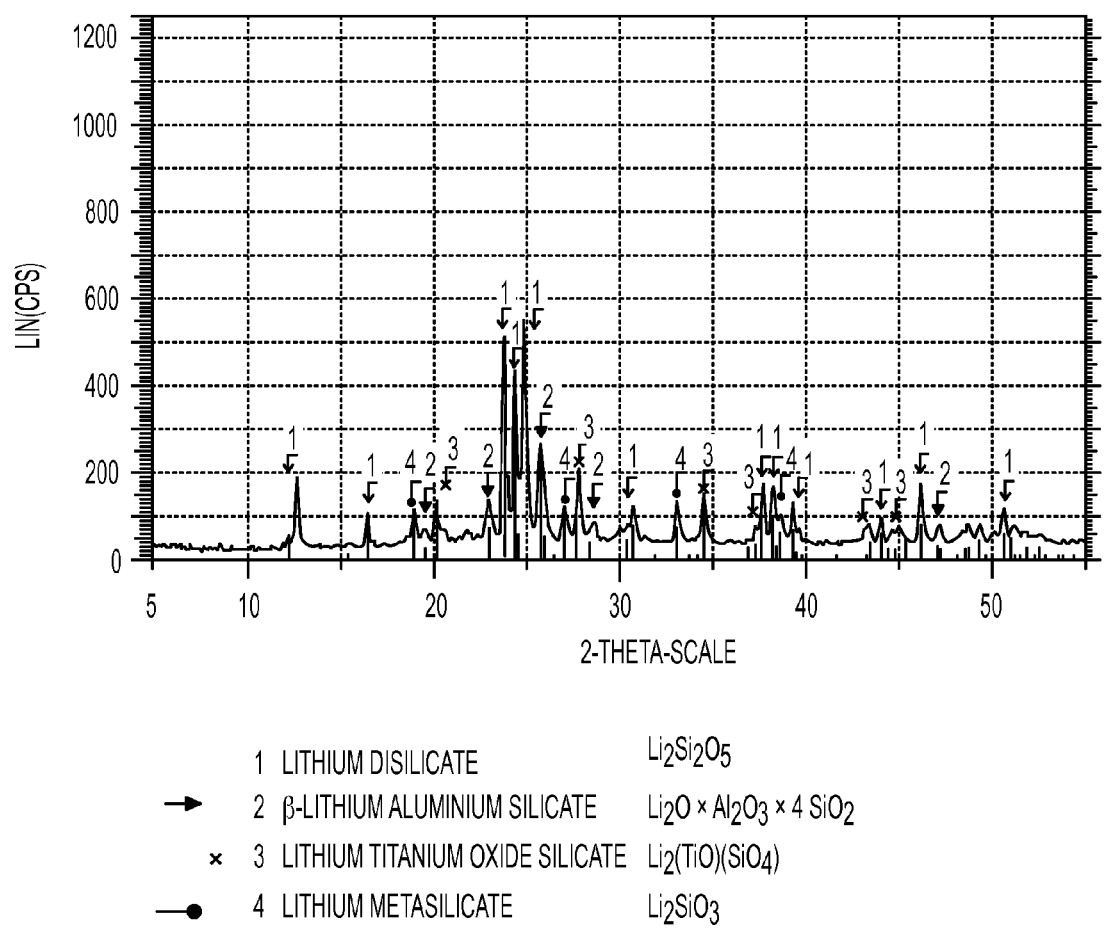
FIG. 3 an XRD of a veneer ceramic according to the invention.

Referring to Table 1 and a temperature of 890° C.±50° C., the examples of veneer ceramics 2, 5 and 7 crystallize to crystal phases of lithium disilicate, beta spodumene, lithium titanium oxide silicate $Li_2(TiO)(SiO_4)$, and lithium metasilicate. The crystallization of lithium disilicate $Li_2Si_2O_5$ is accelerated by the addition of titanium dioxide. FIG. 3 shows the XRD.

What is claimed is:

1. A starting glass for veneer ceramics for dental restorations comprising yttrium-stabilized zirconium dioxide, characterized in that the starting glass comprises the following components:
 a) $SiO_2$ 58.0-74.0% by weight
 b) $Al_2O_3$ 4.0-19.0% by weight
 c) $Li_2O$ 5.0-17.0% by weight
 d) $Na_2O$ 5.3-12.0% by weight
 e) $ZrO_2$ 0.5-6.0% by weight;
 wherein the starting glass is capable upon heat treatment to form the veneer ceramic comprising lithium disilicate as a main crystal phase and
 wherein (i) a weight ratio of $Na_2O:ZrO_2$ is 2.5 to 3.0 and (ii) a weight ratio of $Al_2O_3:ZrO_2$ is 4.0 to 5.0.

2. The starting glass according to claim 1, characterized in that the starting glass is in powdered or non-powder form and the starting glass further comprises powdered crystals.

3. The starting glass according to claim 2, characterized in that the powdered crystals comprise powdered lithium disilicate.

4. The starting glass according to claim 1, characterized in that the starting glass further comprises 0.2 to 8.0% by weight of $TiO_2$.

5. The starting glass according to claim 1, characterized in that the starting glass comprises at least one additive selected from $La_2O_3$, $B_2O_3$, $P_2O_5$, CaO, MgO, ZnO and fluoride in concentrations of up to 4.0% by weight at most.

6. The starting glass according to claim 1, characterized in that the starting glass comprises the following additional components:
 a) $La_2O_3$ 1.0-4.0 percent by weight
 b) $B_2O_3$ 0.0-2.0 percent by weight
 c) MgO 0.0-2.0 percent by weight
 d) CaO 0.0-2.0 percent by weight
 e) ZnO 0.0-2.0 percent by weight
 f) BaO 0.0-1.0 percent by weight
 g) $P_2O_5$ 0.0-2.0 percent by weight
 h) fluoride 0.0-3.0 percent by weight.

7. The starting glass according to claim 1, characterized in that the starting glass comprises oxides of elements Ce, Fe, Mn, Sn, V, Cr, In, and of rare earths Pr, Nd, Sm, Eu, Tb, Dy and Er, individually or in combination as coloring or fluorescing additions.

8. The starting glass according to claim 1, characterized in that the starting glass comprises at least one other alkali oxide for the suppression of crystallization of beta-quartz mixed crystals.

9. The starting glass according to claim 1, characterized in that the $Na_2O$ is contained for the suppression of crystallization of beta-quartz mixed crystals.

10. A starting glass for veneer ceramics for dental restorations comprising yttrium-stabilized zirconium dioxide, characterized in that the starting glass comprises the following components:
 a) $SiO_2$ 58.0-72.0 percent by weight
 b) $Al_2O_3$ 4.0-18.0 percent by weight
 c) $Li_2O$ 5.0-17.0 percent by weight
 d) $Na_2O$ 5.3-11.0 percent by weight
 e) $ZrO_2$ 0.5-5.5 percent by weight
 f) $TiO_2$ 0.2-8.0 percent by weight, and
wherein the starting glass is capable upon heat treatment to form the veneer ceramic comprising lithium disilicate as a main crystal phase.

11. The starting glass according to claim 10, characterized in that the starting glass comprises the following additional components:
 a) $La_2O_3$ 1.0-4.0 percent by weight
 b) $B_2O_3$ 0.0-2.0 percent by weight
 c) MgO 0.0-2.0 percent by weight
 d) CaO 0.0-2.0 percent by weight
 e) ZnO 0.0-2.0 percent by weight
 f) BaO 0.0-1.0 percent by weight
 g) $P_2O_5$ 0.0-2.0 percent by weight
 h) fluoride 0.0-3.0 percent by weight.

12. The starting glass according to claim 11, characterized in that the starting glass comprises oxides of elements Ce, Fe, Mn, Sn, V, Cr, In, and of rare earths Pr, Nd, Sm, Eu, Tb, Dy and Er, individually or in combination, as coloring or fluorescing additions.

13. The starting glass according to claim 10, characterized in that the starting glass comprises at least one other alkali oxide for the suppression of crystallization of beta-quartz mixed crystals.

14. The starting glass according to claim 10, characterized in that the $Na_2O$ is contained for the suppression of crystallization of beta-quartz mixed crystals.

15. The starting glass according to claim 10, characterized in that the starting glass comprises at least one additive selected from $La_2O_3$, $B_2O_3$, $P_2O_5$, CaO, MgO, ZnO and fluoride in concentrations of up to 4.0% by weight at most.

16. A process for veneering dental restorations comprising yttrium-stabilized zirconium dioxide comprising
 providing a starting glass comprising the following components:

a) $SiO_2$ 58.0-74.0% by weight
b) $Al_2O_3$ 4.0-19.0% by weight
c) $Li_2O$ 5.0-17.0% by weight
d) $Na_2O$ 4.0-12.0% by weight
e) $ZrO_2$ 0.5-6.0% by weight; and wherein the starting glass is capable upon heat treatment to form the veneer ceramic comprising lithium disilicate as a main crystal phase;

applying the starting glass onto the yttrium-stabilized zirconium dioxide; and subjecting the glass to heat treatment.

17. A process for veneering dental restorations comprising yttrium-stabilized zirconium dioxide comprising providing a starting glass comprising the following components:

a) $SiO_2$ 58.0-72.0 percent by weight
b) $Al_2O_3$ 4.0-18.0 percent by weight
c) $Li_2O$ 5.0-17.0 percent by weight
d) $Na_2O$ 4.0-11.0 percent by weight
e) $ZrO_2$ 0.5-5.5 percent by weight
f) $TiO_2$ 0.2-8.0 percent by weight, and wherein the starting glass is capable upon heat treatment to form the veneer ceramic comprising lithium disilicate as a main crystal phase;

applying the starting glass onto the yttrium-stabilized zirconium dioxide; and subjecting the glass to heat treatment.

* * * * *